Figure 1:
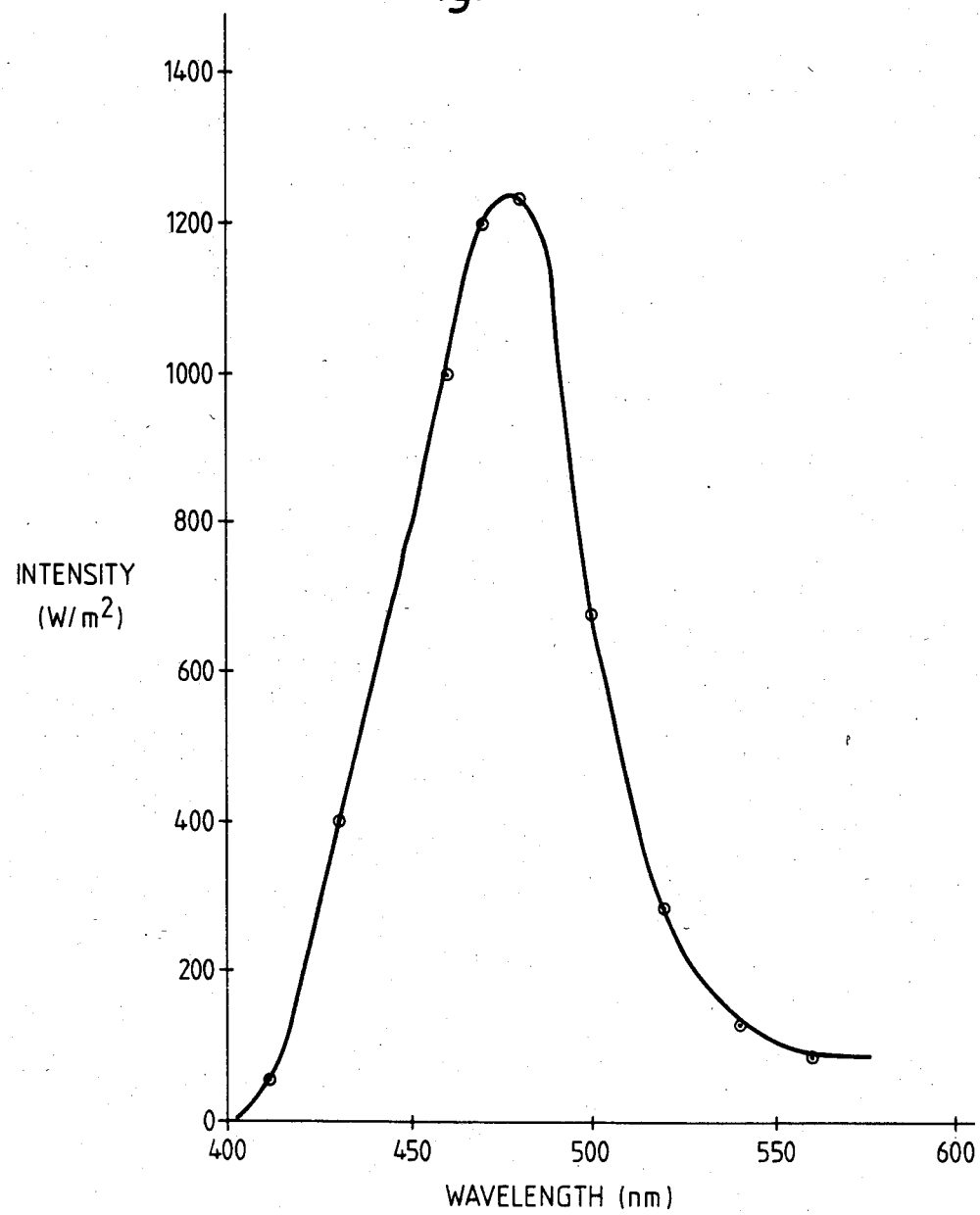

United States Patent [19]

Ratcliffe et al.

[11] Patent Number: 4,602,076
[45] Date of Patent: Jul. 22, 1986

[54] PHOTOPOLYMERIZABLE COMPOSITIONS

[75] Inventors: Maurice J. Ratcliffe, Congleton; Derek J. Shaw, Knutsford; Peter A. Robinson, Chester, all of England

[73] Assignee: Imperial Chemical Industries PLC, London, England

[21] Appl. No.: 772,206

[22] Filed: Sep. 5, 1985

Related U.S. Application Data

[63] Continuation of Ser. No. 468,714, Feb. 22, 1983, abandoned.

[30] Foreign Application Priority Data

Mar. 4, 1982 [GB] United Kingdom ............... 8206317

[51] Int. Cl.⁴ .............................................. C08F 20/10
[52] U.S. Cl. .................................... 522/7; 526/323.1; 526/301; 526/320; 526/323.2; 522/11; 522/13; 522/24; 522/30

[58] Field of Search ............ 526/320, 261, 273, 323.1, 526/323.2, 301; 523/109, 115, 116; 204/159.22, 159.23

[56] References Cited

U.S. PATENT DOCUMENTS

| | | | |
|---|---|---|---|
| 4,243,578 | 1/1981 | O'Sullivan | 523/116 |
| 4,323,591 | 4/1982 | Wendling | 427/53.1 |
| 4,328,325 | 5/1982 | Marquardt | 525/451 |
| 4,347,174 | 8/1982 | Nagase | 523/116 |
| 4,351,853 | 9/1982 | Jochum | 427/2 |
| 4,504,231 | 4/1985 | Koblitz et al. | 433/228 |

FOREIGN PATENT DOCUMENTS 1304112 1/1973 United Kingdom.

Primary Examiner—Christopher A. Henderson
Attorney, Agent, or Firm—Cushman, Darby & Cushman

[57] ABSTRACT

A photopolymerizable composition which comprises at least one ethylenically unsaturated polymerizable monomer, at least one selected ketone and at least one organic peroxide. The compositions are useful in the preparation of adhesives, paints and varnishes particularly in dental applications and exhibit reduced air inhibition on being cured by visible radiation in the range 400 mμ to 500 mμ.

11 Claims, 1 Drawing Figure

PHOTOPOLYMERIZABLE COMPOSITIONS

This is a continuation of application Ser. No. 468,714, filed Feb. 22, 1983, now abandoned.

This invention relates to photopolymerisable compositions and in particular to photopolymerisable compositions which comprise ethylenically unsaturated material and a photosensitive catalyst.

It is known from British patent specification No. 1408265 that compositions comprising an ethylenically unsaturated material and a photosensitive catalyst which comprises an $\alpha$-diketone and an organic amine may be efficiently polymerised by visible light radiation. Polymerisation by visible light has a number of advantages over polymerisation using ultra-violet radiation. It is well known that exposure to the latter can have deleterious effect on health unless precautions are taken to avoid prolonged exposure or use. The problem is particularly acute if the composition is to be used in a medical area such as dentistry because ultra-violet radiation can damage gum tissue. Levels of radiation output from an ultra-violet source are often difficult to control so that exposure times for a satisfactory level of polymerisation can vary so leading to irregular properties in the polymerised material.

Polymerisation using conventional amine-peroxide catalyst systems are unattractive because the components have to be mixed at a point of use rather than premixed in order to avoid premature polymerisation; such a procedure can lead to inaccurate amounts of components being mixed which again can lead to irregular and unpredictable polymerisation. Polymerisation can be effected at elevated temperatures but this is not appropriate for sensitive substrates and adds to cost of plant and associated equipment.

Polymerisation using visible light suffers from none of the above disadvantages. Whilst the use of $\alpha$-diketone - organic amine visible light cure catalyst system is generally very satisfactory in the polymerisation of ethylenically unsaturated materials, it has now been found that the inclusion of organic peroxide in the catalyst system containing selected ketones, even in the absence of organic amine, unexpectedly improves the quality of cure provided by visible light radiation. The improvement manifests itself by reduced air inhibition of polymerisation. Air inhibition manifests itself in lack of cure of a thin layer of polymerisable material adjacent to the air. It results in a coating having a sticky surface whilst material below that layer might be hard and fully cured.

It has been suggested in U.S. Pat. No. 4,024,276 that the use of phenanthraquinone as photosensitive catalyst in a composition containing an ultra-violet hiding filler such as titanium dioxide leads to good cure of the interior of a coating of the composition on irradiation with a mixture of visible and ultra-violet radiation. Air inhibition at the surface is said to be improved by the addition of a ketone having triplet energy of 54 kilocalories per mole to 72 kilocalories per mole; preferred such ketones are phenylgloxylates. In U.S. Pat. No. 4,097,994 there are described dental restorative compositions containing a specific polymerisable resin, an organic peroxide catalyst and Michler's ketone as photosensitive catalyst. These are said to show rapid cure on exposure to ultra-violet irradiation and to form a tack free surface. That U.S. patent specification also states that other ketones than Michler's ketone, such as benzil and furil are ineffective in the presence of oxygen. British patent specification No. 1304112 describes the polymerisation of unsaturated polyesters by argon swirl flow plasma arc using a benzil/benzoyal peroxide catalyst; this catalyst is shown to be less efficient than benzoyl peroxide alone.

It has been found unexpectedly that on irradiation with visible light, selected ketones are particularly effective photosensitive catalysts and lead to improved cure in the presence of air.

According to the present invention a photopolymerisable composition is provided which comprises at least one ethylenically unsaturated polymerisable monomer, at least one ketone selected from fluorenone and camphorquinone and their substituted derivatives and at least one organic peroxide.

According to a further embodiment of the present invention, a photopolymerisable composition is provided which comprises at least one ethylenically unsaturated polymerisable monomer, at least one ketone selected from fluorenone, benzil and camphorquinone and their substituted derivatives, at least one reducing agent capable of reducing the ketone when the latter is in an excited state and at least one organic peroxide.

The compositions of the present invention have a variety of uses such as coatings for a range of substrates, adhesives, paints and varnishes, they are particularly useful for dental applications. Such applications include dental glazes, fissure sealants, bonding agents and orthodontic cements.

The compositions of the present invention will generally be used in the absence of filler but small quantities of opaque organic and/or organic filler, e.g. up to 10% by weight based on the total composition may be included to provide a special effect, e.g. colour, abrasion resistance. Preferably inclusion level of filler has no substantial effect on viscosity characteristics of the composition. Larger quantities of fillers which are transparent or substantially transparent in the composition because of for example refractive index matching with the polymerisable material are also comprehended. For dental applications, it is essential that the composition be liquid so that the composition in an unpolymerised state flows over an etched surface without having so low a viscosity that the composition runs off the tooth surface into the patient's mouth.

The polymerisable ethylenically unsaturated material is suitably at least one monomer containing ethylenic unsaturation in a terminal group. For example, the ethylenically unsaturated material may be one or more monomers selected from vinyl monomers, allyl monomers and vinylidene monomers.

Suitable vinyl monomers which may be polymerised include, for example, vinyl esters, aromatic vinyl compounds and vinyl nitriles. By the term "vinyl monomers" we mean monomers containing the group $CH_2=C(R)$—where R is hydrogen or hydrocarbyl.

Vinyl esters suitable for use in the method of our invention include, for example, vinyl acetate and esters of acrylic acid having the structure $CH_2=CH-COOR^7$, where $R^7$ is an alkyl, aryl, alkaryl, aralkyl or cycloalkyl group. For example, $R^7$ may be an alkyl group having from 1 to 20, and preferably 1 to 10 carbon atoms. Particular vinyl esters which may be mentioned include, for example, methyl acrylate, ethyl acrylate, n- and isopropyl-acrylates, and n-, iso- and tertiary butyl acrylates.

Other suitable vinyl esters include, for example, esters of the formula

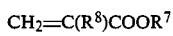

where $R_8$ is methyl. In the ester of formula

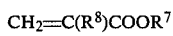

$R^7$ and $R^8$ may be the same or different.

Particular vinyl esters which may be mentioned include, for example, methyl methacrylate, ethyl methacrylate, n- and isopropyl-methacrylate, and n-, iso- and tertiary butyl methacrylate. Suitable aromatic vinyl compounds include, for example, styrene and derivatives thereof, e.g. α-alkyl derivatives of styrene, e.g. α-methyl styrene, and vinyl toluene.

Suitable vinyl nitriles include, for example, acrylonitrile and derivatives thereof, e.g. methacrylonitrile.

ther suitable vinyl monomers include vinyl pyrrollidone, and hydroxyalkyl acrylates and methacrylates, e.g. hydroxyethyl acrylate, hydroxypropylacrylate, hydroxy methacrylate and hydroxypropylmethacrylate.

The ethylenically unsaturated material may include at least one ethylenically unsaturated polymer, suitably in combination with at least one ethylenically unsaturated monomer.

Where the ethylenically unsaturated material is a solid then it may be convenient, in order to produce a liquid composition, to include in the composition sufficient amount of a suitable diluent. The diluent should, of course, have little or no inhibiting effect on the polymerisation of the ethylenically unsaturated material in the composition.

The polymerisable material includes those referred to above but is preferably liquid ethylenically unsaturated material such as vinyl urethane for example those described in British patent specification Nos. 1352063, 1465097, 1498421 and German Offenlegungsschrift No. 2419887 or the reaction product of a diol such as glycol but particularly a bisphenol with a glycidyl alkacrylate such as those described for example in U.S. Pat. Nos. 3,066,112 and 4,131,729 (the disclosure in these specifications are incorporated herein by way of reference).

A preferred reaction product of a glycidyl alkacrylate and a diol has the formula:

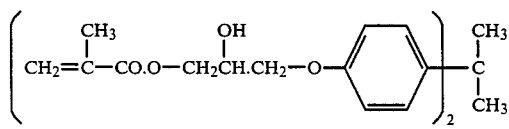

Preferred vinyl urethanes described in the aforesaid British patent specification and German Offenlegungsschrift are the reaction product of a urethane prepolymer and an ester of acrylic or methacrylic acid with a hydroxy alkanol of at least 2 carbon atoms, the urethane prepolymer being the reaction product of a diisocyanate of the structure OCN-$R^1$-NCO and a diol of the structure HO-$R^2$-OH wherein $R^1$ is a divalent hydrocarbyl group and $R^2$ is the residue of a condensate of an alkylene oxide with an organic compound containing two phenolic or alcoholic groups.

Other suitable vinyl urethanes include those made by the reaction of alkyl and aryl, preferably alkyl, diisocyanates with hydroxy alkyl acrylates and alkacrylates such as those described in British patent specification Nos. 1401805, 1428672, and 1430303 (the disclosures of which are included herein by way of reference).

Liquid ethylenically unsaturated monomers (the polymers of which should be water insoluble) suitable as polymerisable materials include vinyl monomers, e.g. vinyl esters such as n-hexyl, cyclohexyl and tetrahydrofurfuryl acrylates and methacrylates. The monomers should have low toxicity.

Polyfunctional monomers are also suitable as polymerisation materials vinyl monomers, that is, monomers containing two or more vinyl groups. Suitable monomers include, for example, glycol, dimethacrylate, diallyl phthalate, and triallyl cyanurate.

A preferred polymerisable material comprises a mixture of vinyl urethane or glycidyl alkacrylate and 25% to 150% by weight of vinyl urethane or glycidyl alkacrylate of at least one polyfunctional monomer hereinbefore described.

Ketones suitable for use in the compositions of the present invention also show some photosensitive catalytic action on their own without the presence of organic peroxide. Such activity of the ketone is enhanced by the addition of an organic amine as described in the aforesaid British patent specification No. 1408265. Accordingly the present ketones are selected from fluorenone, benzil and camphorquinone and their derivatives which in admixture with a similar amount of organic amine which is capable of reducing that ketone when the latter is in an excited state, but in the absence of organic peroxide catalyst cure an ethylenically unsaturated material. Evidence of cure may be conveniently detected by examining the change in viscosity of a mixture of the ethylenically unsaturated material containing the ketone and organic amine at a level of 1% by weight of the polymerisable material using an oscillating rheometer, sample thickness 0.5 mm., whilst the mixture is being irradiated with light having wavelength in the range 400 to 500 mμ. Such an examination may be carried out using the method described in British Standard 5199:1975, paragraph 6.4 provided that provision is made to allow visible light to be directed onto the mixture. Preferably the ketone has a cure time of less than 15 minutes at a radiation level of 1000 w/m² as measured at 470 mμ, bandwidth ±8 mμ, for example using a Macam Radiometer (Macam Photometrics Ltd., Edinburgh, Scotland).

Ketones suitable for the present invention are fluorenone, benzil and camphorquinone and their substituted derivatives. They should ideally have low volatility at ambient temperature. By the term "substituted derivatives" is meant that one or more of the hydrogen atoms in the respective unsubstituted ketones is/are substituted by hydrocarbyl or substituted hydrocarbyl groups, provided that the substituents do not substantially inhibit the cure, of the resulting composition. Examples are lower alkyl (C1-6), halo-, nitro-. Such substituted ketones include for example
p,p'-dialkoxy benzil e.g. p,p'-dimethoxy benzil
p,p'-dihalobenzil e.g. p,p'-dichlorobenzil
p,p'-dialkyl benzil e.g. p-tolil and p,p'-dinitrobenzil
fluorenone-2-carboxylic acid
fluorenone-4-carboxylic acid
A preferred ketone is camphorquinone.

The ketone may, for example, be present in the composition in a concentration in the range 0.01% to 2% by weight of the polymerisable material in the composition although concentrations outside this range may be used if desired. Preferably the α-diketone is present in a concentration of 0.1% to 1% by weight of the ethylenically unsaturated materials in composition. The ketone should be soluble in the polymerisable material and the above concentrations refer to solution concentrations.

The organic peroxides suitable for use in the present composition include those having the formula

R—O—O—R in which the groups R which may be the same or different, are hydrogen, alkyl, aryl, or acyl groups, no more than one of the groups R being hydrogen. The term acyl means groups having the formula $R^3$—CO— in which $R^3$ is an alkyl, aryl, alkoxy or aryloxy group. The terms alkyl and aryl have the definitions given hereinbefore for the groups A and include substituted alkyl and aryl.

Examples of organic peroxides suitable for use in the composition of the present invention include diacetyl peroxide, dibenzoyl peroxide, ditertiary butyl peroxide, dilauroyl peroxide, tertiary butyl perbenzoate, ditertiary butyl cyclohexyl perdicarbonate.

The organic peroxide may be, for example, present in the composition in the range 0.1% to 20%, preferably 0.5% to 5%, weight of the polymerisable material in the composition although concentrations outside this range may be used if desired.

The reactivity of a peroxide is often measured in terms of its half life temperature, i.e. within ten hours at that temperature half of the oxygen has been made available.

The peroxides in the present compositions preferably have ten hour half life temperatures of less than 150° C., more preferably less than 110° C.

The rate at which the composition of the invention cures under the influence of visible light can be increased by incorporation into the composition a reducing agent which is capable of reducing the ketone when the latter is in an excited state. Such reducing agents are described in German Offenlegungsschrift No. 251048 and are preferably organic amines having the formula $R^4_3N$ where the groups $R^4$, which may be the same or different, are hydrogen atoms, hydrocarbyl groups, substituted hydrocarbyl groups or groups in which two units $R^4$ together with the nitrogen atom form a cyclic ring system, no more than two of the units $R^4$ being hydrogen atoms and where the nitrogen atom is attached directly to an $R^4$ group which is aromatic, at least one of the other units $R^4$ has a $$\begin{array}{c} | \\ -C- \\ | \\ H \end{array}$$

group attached to the nitrogen atom. The reducing agent is preferably present in the composition in concentration in the range 0.01% to 2% by weight of the polymerisable material although concentrations outside this range may be used if desired.

Mixing of the components may be effected by stirring together the polymerisable material and any filler. It may be useful to dissolve the catalyst components first in the polymerisable material; the polymerisable material may conveniently be diluted with a suitable diluent so as to improve solution of the catalyst components. When mixing has been effected the diluent may be removed if desired, e.g. by evaporation.

Because the photosensitive catalyst renders the polymerisable material and monomer sensitive to light in the 400 mμ to 500 mμ visible range, that part of the preparation of the present composition in which photosensitive catalyst is added and subsequent manipulation, e.g filling of containers should be carried out in the substantial absence of light in that range. Most conveniently, the preparation can be carried out using light outside that range for example under that emitted by sodium vapour electric discharge lamps.

In accordance with a further embodiment of the present invention a curing process is provided which comprises irradiating the composition of the invention with visible radiation having wavelength between 400 mμ and 500 mμ. The process may be carried out at any convenient temperature provided that the composition does not crystallize and fragment, the temperature thereby being too low, or unduly volatile, the temperature thereby being too high. Preferably the process is carried out at ambient temperatures, i.e. between 15° C. and 40° C.

It is envisaged that a substrate will be coated with the present composition and if large then passed by or under a visible light source. If the coated substrate is only small or part of a large article, then conveniently the composition is cured from a portable light source.

A dental composition according to the present invention is preferably packed in single small containers (e.g. 10 g. capacity) so as to facilitate handling in the surgery and reduce the risk of inadvertent curing by for example stray light. However, where the catalyst contains an amine, the present composition may if desired be packed in two containers, one containing peroxide and the other the amine, together with such other components of the mixture such that when the contents of the two containers are mixed, e.g. in a dentist surgery, the present composition is produced; nevertheless packaging in a single container is preferred.

For cosmetic purposes, such a dental composition may have a stained, coloured or natural tooth appearance and hence the present composition may include small quantities of pigments, opalescent agents and the like. The composition may also include small quantities of other materials such as anti-oxidants and stabilisers provided that they do not substantially affect cure.

The invention is illustrated with reference to the following Examples:

EXAMPLE 1

Condensate (35.2 g. 0.1 mole) obtained by reacting 2,2-bis-(4-hydroxyphenyl)propane and propylene oxide in a molar ratio of 1:2 (oxypropylated Bisphenol A) was dissolved in approximately 100 g. of methylene dichloride and the resulting solution was added dropwise to a solution of 33.6 g. (0.2 mole) of hexamethylene diisocyanate in 100 g. of methylene dichloride under an atmosphere of nitrogen gas. 4 drops of dibutyl tin dilaurate (available as "Mellite" 12, "Mellite" is a registered trade mark) were added as catalyst. The mixture was stirred under nitrogen for 1 hour after which it was heated under reflux conditions for 9 hours. The mixture was then cooled and a solution of 29 g. (0.2 mole) of hydroxypropyl methacrylate in 100 g. of methylene dichloride was added after which the mixture was heated under reflux conditions for 3 hours. The hydroxypropyl ester comprised isomers in weight ratio 2-hydroxypropyl (2.6 parts) to 1-methyl-2-hydroxyethyl) (1 part). To the mixture of vinyl urethane and methylene chloride was added triethylene glycol dimethacrylate sufficient to produce polymerisable material containing 50% by weight vinyl urethane and 50% by weight of triethylene glycol dimethacrylate. The methylene chloride was removed by distillation.

Catalyst mixture having the composition given below was prepared by dissolving the components in methylene chloride and the solution was added to the polymerisable mixture. This addition and subsequent manipulative procedure with the mixture were carried out under sodium vapour discharge light.

Air inhibition on subsequent polymerisation using visible light was investigated by a method based on that of Ruyter, Acta Odontol Scand. 1981, 39, 27–32. A drop of the above mixture was placed on a microscope slide over the top of which was placed another slide so that mixture was trapped between the slides to provide a mixture layer having thickness between 10 and 50 μm. The layer was then irradiated for periods shown in the following Table using a tungsten - halogen light source having intensity 1000 w/m$^2$ at wavelength of 470 nm ±8 nm. The spectral distribution of the light source is given in FIG. 1. Using a travelling microscope, the thickness of unpolymerised layer was measured. Four samples of each mixture were used and four readings were taken from each sample; the mean with standard deviation is presented for each set of readings in the Table.

| Catalyst | Thickness (μm) of air inhibited layer after cure for | | |
|---|---|---|---|
| | 2 sec. | 10 sec. | 20 sec. |
| 0.3% CQ | | 16.9 ± 3.79 | 9.75 ± 1.54 |
| 0.3% CQ 0.3% DMAEM | 15.5 ± 2.28 | 12.71 ± 1.94 | 7.25 ± 0.97 |
| 0.3% CQ 0.3% DMAEM 1.47% TPB | 8.92 ± 1.26 | 6.8 ± 1.39 | 6.23 ± 1.36 |
| 0.25% CQ 2.4% TPB | | 7.80 ± 0.79 | |

In the Table, percentages are expressed by weight based on polymerisable material.
CQ—camphorquinone
DMAEM—dimethylamino ethyl methacrylate
TPB—tertiary butyl perbenzoate The results show that inclusion of peroxide is associated with a reduction of the thickness of the air inhibited layer.

EXAMPLE 2

Compositions were prepared and evaluated as described in Example 1 except that the catalyst mixture used was that given in the table below:

| Catalyst | Thickness (μm) of air inhibited layer after cure for | |
|---|---|---|
| | 90 secs. | 40 secs. |
| (a) 0.25% F | 14.7 ± 1.25 | 19.3 ± 1.34 |
| (b) 0.25% F 0.5% DMAEM | 10.0 ± 1.24 | 13.2 ± 1.55 |
| (c) 0.25% F 0.5% DMAEM | 8.3 ± 0.48 | 10.8 ± 1.04 |
| 2.4% TBP | | |

In the table percentages are expressed by weight based on polymerisable material; symbols are those used in Example 1 and F is fluorenone.

The results show that the inclusion of peroxide is associated with a reduction of the thickness of the air inhibited layer.

By way of comparison, compositions similar to a, b and c above in which phenanthrenequinone was used in place of fluorenone exhibited no similar reduction in air inhibited layer after cure for 40 seconds.

EXAMPLE 3

Compositions were prepared and evaluated as described in Example 1 except that the light source had intensity of 1250 w/m$^2$ at a wavelength of 470 nm±8 nm.

| Catalyst | Thickness of air inhibited layer (μm) after cure for 10 secs. |
|---|---|
| 0.25% BZ 0.5% DMAEM | 13.90 ± 2.60 |
| 0.25% BZ 0.5% DMAEM 2.4% Bz$_2$O$_2$ | 7.88 ± 0.60 |
| 0.25% BZ 2.4% Bz$_2$O$_2$ | 9.73 ± 0.90 |

In the table, percentages are expressed by weight based on polymerisable material; symbols are those used in Example 1 and BZ is benzil, Bz$_2$O$_2$ is benzoyl peroxide.

We claim:

1. A photopolymerisable composition which comprises at least one ethylenically unsaturated polymerisable monomer, at least one ketone selected from fluorenone and comphorquinone and their substituted derivatives and at least one organic peroxide, said composition being characterized by its improved cure on irradiation with visible light at ambient temperature and in the presence of air.

2. A photopolymerisable composition which comprises at least one ethylenically unsaturated polymerisable monomer, at least one ketone selected from fluorenone, benzil and camphorquinone and their substituted derivatives, at least one reducing agent capable of reducing the ketone when the latter is in an excited state and at least one organic peroxide, said composition being characterized by its improved cure on irradiation with visible light at ambient temperature and in the presence of air.

3. A photopolymerisable composition according to claim 2 in which the reducing agent concentration is in the range 0.01% to 2% by weight of the composition.

4. A photopolymerisable composition according to claim 2 in which the reducing agent is an organic amine having the formula $R^4_3N$ where the grouos $R^4$, which may be the same or different, are hydrogen atoms, hydrocarbyl groups, substituted hydrocarbyl groups or groups in which two units $R^4$ together with the nitrogen atom form a cyclic ring system, no more than two of the units $R^4$ being hydrogen atoms and where the nitrogen atom is attached directly to an R⁴ group which is aromatic, at least one of the other units R⁴ has a

group attached to the nitrogen atom.

5. A photopolymerisable composition according to either claim 1 or 2 in which the ethylenically unsaturated polymerisable monomer comprises a diacrylate or dimethacrylate.

6. A photopolymerisable composition according to either claim 1 or 2 in which the ketone concentration is in the range 0.01% to 2% by weight of the composition.

7. A photopolymerisable composition according to either claim 1 or 2 in which the organic peroxide concentration is in the range 0.1% to 20% by weight of the composition.

8. A photopolymerisable composition according to either claim 1 or 2 in which the organic peroxide has a ten hour half life temperature of less than 150° C.

9. A photopolymerisable composition according to either claim 1 or 2 in which the ketone is camphorquinone.

10. A photopolymerisable composition according to claim 9 in which the organic peroxide is tertiarybutyl perbenzoate.

11. A photopolymerisable composition which comprises at least one ethylenically unsaturated polymerisable monomer, at least one ketone selected from fluorenone and camphorquinone and their substituted derivatives, said ketone concentration is in the range 0.10% to 2% by weight of the composition, and at least one organic peroxide, said organic peroxide concentration is in the range of 0.1% to 20% by weight of the composition, said composition being characterized by its improved cure on a radiation with visible light at ambient temperature in the presence of air.

* * * * *